United States Patent
Kane et al.

(10) Patent No.: US 10,493,300 B2
(45) Date of Patent: Dec. 3, 2019

(54) PROTON THERAPY BEAM-SHARING PANEL DISPLAY AND CONTROLS

(75) Inventors: Richard Kane, Los Altos, CA (US); Brian Spatola, Huntington Beach, CA (US); Julie Clift, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1417 days.

(21) Appl. No.: 13/460,274

(22) Filed: Apr. 30, 2012

(65) Prior Publication Data

US 2013/0086500 A1    Apr. 4, 2013

Related U.S. Application Data

(60) Provisional application No. 61/542,092, filed on Sep. 30, 2011.

(51) Int. Cl.
*G06F 3/048* (2013.01)
*A61N 5/10* (2006.01)

(52) U.S. Cl.
CPC .... *A61N 5/1079* (2013.01); *A61N 2005/1074* (2013.01); *A61N 2005/1087* (2013.01)

(58) Field of Classification Search
CPC .............................. A61N 5/1077; A61N 5/1079
USPC .......................................... 715/771; 709/200
See application file for complete search history.

(56) References Cited

U.S. PATENT DOCUMENTS

| | | | |
|---|---|---|---|
| 5,511,549 A | 4/1996 | Legg et al. | |
| 5,809,106 A * | 9/1998 | Kitade | H01J 35/101 378/117 |
| 6,717,162 B1 * | 4/2004 | Jongen | A61N 5/1042 250/492.1 |
| 7,012,267 B2 | 3/2006 | Moriyama et al. | |
| 2002/0099363 A1 * | 7/2002 | Woodward | A61F 9/0079 606/5 |
| 2003/0179756 A1 * | 9/2003 | Cain | H04B 7/0491 370/395.42 |
| 2004/0098445 A1 | 5/2004 | Baumann et al. | |
| 2004/0173763 A1 * | 9/2004 | Moriyama | A61N 5/10 250/492.1 |
| 2004/0200983 A1 * | 10/2004 | Fujimaki | A61N 5/10 250/492.3 |
| 2005/0029472 A1 * | 2/2005 | Ueno | A61N 5/10 250/492.1 |
| 2006/0017009 A1 * | 1/2006 | Rink | G01T 1/161 250/484.5 |
| 2007/0018121 A1 * | 1/2007 | Leyman et al. | ............ 250/494.1 |
| 2012/0253545 A1 * | 10/2012 | Tachibana | A61N 5/1079 700/306 |

* cited by examiner

*Primary Examiner* — Daeho D Song

(57) ABSTRACT

Systems and methods are described herein to provide a user-interface to visualize and control a beam request panel for requesting allocation of usage of a shared therapy beam. The user interface allows a user to visualize a beam request queue, to request the shared therapy beam for treatment, to estimate when a beam request will be fulfilled, and to cancel a beam request if needed.

24 Claims, 7 Drawing Sheets

PROTON THERAPY BEAM-SHARING PANEL DISPLAY AND CONTROLS

CLAIM OF PRIORITY

This application claims priority to U.S. Provisional Patent Application No. 61/542,092, entitled "Proton Therapy Beam-Sharing Panel Display and Controls," and filed Sep. 30, 2011.

TECHNICAL BACKGROUND

Proton therapy is a type of external beam radiation therapy characterized for using a beam of protons to irradiate diseased tissue. The chief advantage of proton therapy over other conventional therapies such as X-ray or neutron radiation therapies is the ability to administer treatment dosages three-dimensionally by specifying the depth (i.e., limiting the penetration) of applied radiation, thereby limiting the inadvertent exposure of un-targeted cells to the potentially harmful radiation. This enables proton therapy treatments to more precisely localize the radiation dosage relative to other types of external beam radiotherapy. During proton therapy treatment, a particle accelerator, such as a cyclotron, is used to generate a beam of protons from, for example, an internal ion source located in the center of the cyclotron. The protons in the beam are accelerated (via a generated electric field), and the beam of accelerated protons is subsequently "extracted," magnetically directed through a series of interconnecting tubes (called the beamline), often through multiple chambers, rooms, or even floors of a building, and finally applied to a target area/subject in a target treatment room.

Due to the high cost of manufacturing, installing, and servicing a proton particle accelerator (such as a cyclotron), even clinical institutions which provide proton beam therapy services typically will have only one cyclotron on the premises. As a result, this requires that usage of a cyclotron at a clinical facility for proton therapy be shared—amongst its requesting proton therapy practitioners, for example. For clinical facilities with several treatment rooms, the proton beam can be distributed (via magnetic directing) to each treatment room or suite of rooms as needed. Unfortunately, conventional sharing systems for a central beam-source can be overly simple, inefficient, and uncertain. For example, conventional proton beam-sharing systems may require dedicated engineers to monitor beam allocation and to re-allocate the beam to other treatment rooms. Naturally, this would require additional lines of communication (e.g., between the engineer and therapist for a treatment room, and even between engineers of different treatment rooms) and user attention—which may result in adverse effects, such as delays, inefficiency, and simple human error.

Alternative proton beam-sharing systems may include a centralized system that allows a plurality of therapists to semi-automatically request usage of a generated proton beam. However, these systems provide very limited visibility for the requesting practitioners, typically only indicating whether the proton accelerator is in use, and perhaps which treatment room the proton beam is currently being directed to. Even systems that allow a simple queuing generally do not provide enough information for a therapist to estimate, with any degree of granularity, when the proton beam may be available for the therapist to use. A therapist must therefore closely monitor the interface to determine when an appropriate request may be made (e.g., when the proton accelerator is idle, and when the beam has been granted to them). Naturally, this uncertainty can also result in significant inefficiency, delay, and patient discomfort/inconvenience.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

To overcome the difficulties inherent in conventional proton therapy sharing systems, new techniques for automating and visualizing these procedures are herein provided. A control system is described which provides a user interface that displays a clear, graphical indication of relevant fields of data for a proton therapy beam queue. The user interface allows a user to visualize the beam queue, request the beam for treatment, see an estimation when the request will be granted and/or fulfilled, and cancel a beam request if necessary. In further embodiments, the system allows a therapist to request usage of a generated proton therapy beam with as few as one user-actuation.

Further embodiments extend the ability to request a prioritized usage of the generated proton therapy beam to possibly being assigned an advanced position for the requesting treatment room in the beam queue, based on factors such as urgency, for example. Additional information, such as the progress of a treatment session for which the beam is currently in use, the status and priority of other requesting rooms, and precise calculations for an estimated time until a treatment room is able to receive the generated proton beam are also clearly and intuitively visualized. According to one embodiment, the calculations for the estimated time until a treatment room will receive the generated proton beam will be adjusted and visually reflected dynamically in real-time, in the event that requests with (higher) priority are subsequently added.

According to a second aspect of the invention, a method for requesting proton beam usage in a visualized queue is described. Proton beam allocation to each treatment room is automated according to the visualized queue, thereby allowing a practitioner or therapist to prepare a patient or target treatment area accurately and efficiently.

By utilizing the systems and methods described above, a user is able to intuitively and efficiently perform the requisite functions for proton beam management in a shared beam facility. These functions—all of which can be performed within a single, integrated user-interface—include visualization of the beam queue, submission of requests for the beam for treatment, estimations of when the request will be fulfilled and cancellations of the request.

BRIEF DESCRIPTION OF DRAWINGS

The accompanying drawings, which are incorporated in and form a part of this specification, illustrate embodiments of the disclosure and, together with the description, serve to explain the principles of the presently claimed subject matter:

DETAILED DESCRIPTION

Figure 1:
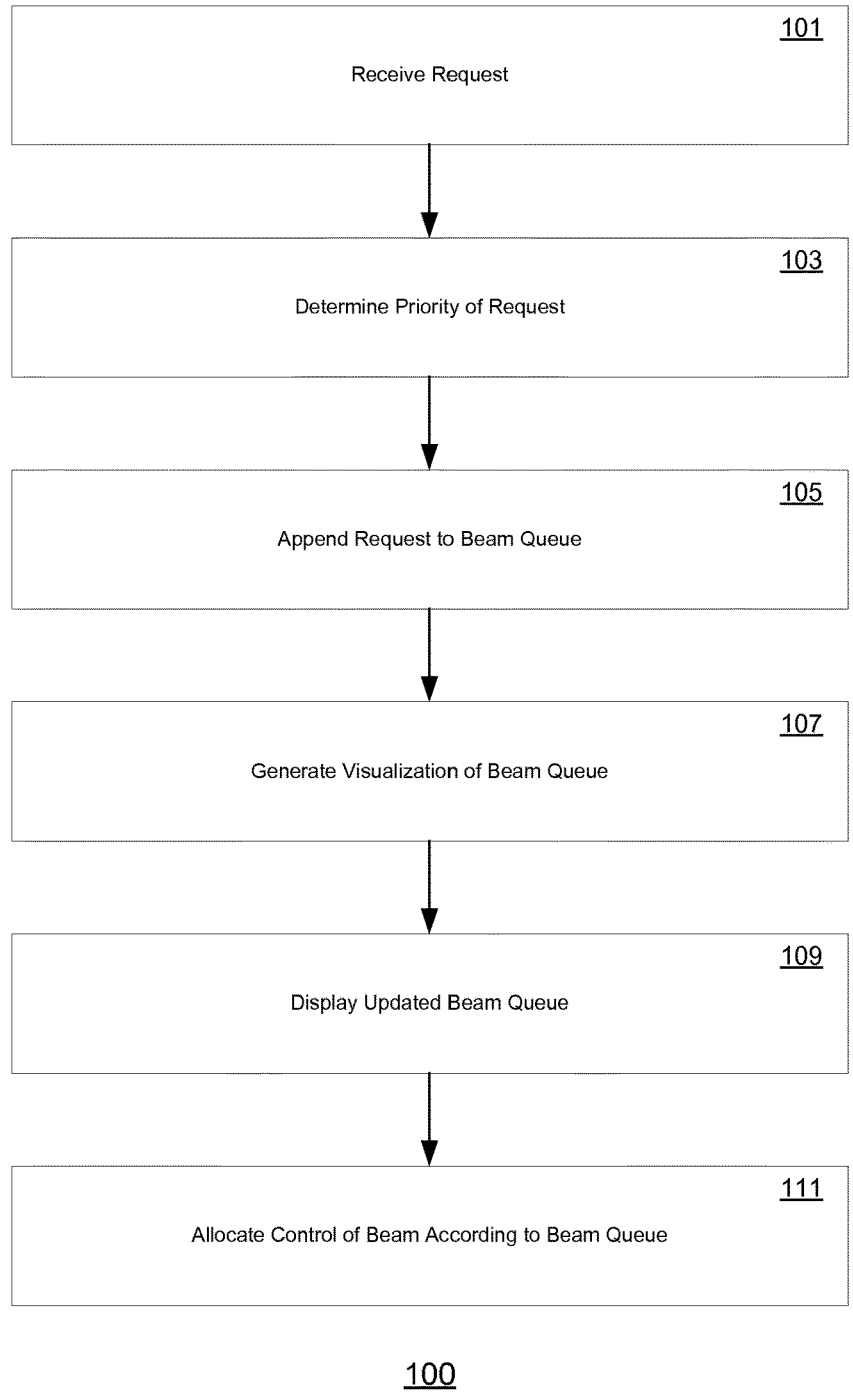
FIG. 1 depicts a flowchart of a process for providing beam-sharing functionality in an integrated control panel, in accordance with embodiments of the present disclosure.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known processes, procedures, components, and circuits have not been described in detail as not to unnecessarily obscure aspects and features of the subject matter.

Portions of the detailed description that follow are presented and discussed in terms of a process. Although operations and sequencing thereof are disclosed in a figure herein (e.g., FIG. 1) describing the operations of this process, such operations and sequencing are exemplary. Embodiments are well suited to performing various other operations or variations of the operations recited in the flowchart of the figure herein, and in a sequence other than that depicted and described herein.

Some portions of the detailed description are presented in terms of procedures, operations, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed operation, logic block, process, etc., is here, and generally, conceived to be a self-consistent sequence of operations or instructions leading to a desired result. The operations are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

While the following example configurations are shown as incorporating specific, enumerated features and elements, it is understood that such depiction is exemplary. Accordingly, embodiments are well suited to applications involving different, additional, or fewer elements, features, or arrangements.

The claimed subject matter is directed to a beam request system which provides a user interface that displays a clear, graphical indication of relevant fields of data for a proton therapy beam queue. In an embodiment, the beam request system may be implemented as one or more instances of an integrated beam request panel or display, executed as computer-implemented graphical interfaces associated with a like number of treatment rooms. The beam request panel as described may be configured to provide a distributed system to provide customized graphical visualizations of a queue of beam requestors, and integrated displays and controls to submit a request for control of the beam. For example, each instance of the integrated beam request panel may comprise a request interface through which a user is able to submit a request for use of a shared proton beam in an associated treatment room for a duration; and a graphical indicator of the beam request (e.g., "beam request display") customized for the particular user. According to further embodiments, the beam request panel may contain functionality to submit a request for usage of the beam with different priorities and scopes of usage.

According to still further embodiments, the beam request panel (through the beam request display, for example) may also graphically present estimated wait times and related queue status information for requests submitted by a user through the beam request interface associated with the beam request display. The presented estimated wait times may be used by the therapist and/or beam administrator to determine the appropriate time to begin preparing the patient or beam subject for treatment. In addition, the beam request interface may also provide controls for the user (i.e., the beam requestor) to cancel a pending beam request, or a beam control grant. According to some embodiments, the display contents and controls indicate request functions and beam request statuses via graphical or numeric means. According, the display and integrated controls can be significantly, if not completely, language-independent.

According to embodiments, the beam request panel does not directly provide functionality for controlling the beam, or the beam delivery. According to such embodiments, control of beam delivery is accomplished through a separate and distinct device dedicated to beam delivery control. The beam request panel discussed herein is directed to requesting a turn with the beam. Once usage of the beam has been granted to a viewing terminal, treatment personnel can use a separate and distinct device (e.g., a "treatment keypad") to deliver the beam or terminate beam delivery, etc.

As recited herein, a beam is defined as a proton therapy beam that is shared amongst a plurality of treatment suits in a treatment facility to apply proton beam treatments in discrete treatment sessions. Each session may itself contain one or more treatment fields. These fields may be identified separately, collectively, or associated in one or more groups. According to an embodiment, only one treatment suite can use the beam at a time. Accordingly, beam requesters are able to request that use of the beam be granted to them through a user interface of a control panel (more specifically, an instance of the integrated control panel) corresponding to a treatment room. In some embodiments, the control panel may be executed on a computing system within, or immediately adjacent to, a treatment room. In further embodiments, access to the beam control panel may be restricted to authorized personnel only. Security features may be integrated within the system to require proper credentials—such as unique and identifying user-ids and/or passwords) before the beam control panel may be displayed and/or accessed by a user.

As recited herein, a treatment facility is defined as a physical treatment complex consisting of multiple treatment suites. A treatment suite is defined as one of multiple areas within a facility where the beam can be used. Each treatment suite may consist of a treatment room, treatment control room, imaging alcove and various treatment preparation rooms.

As recited herein, a therapy team is described as one or more members of the group of therapists or proton therapy practitioners assigned to a given treatment suite for one or more treatment sessions. A beam requester is defined as a treatment suite team member that can potentially request the beam. Note that there may also be non-treatment areas that can request to use the beam (e.g., research, maintenance, or service areas). These can also be beam requestors, or treatment suites. A beam request is defined herein as a request to use the beam that is either waiting to be fulfilled or is presently being fulfilled. A beam sharing queue or beam queue is defined herein as an order in which beam requestors have requested the beam for a treatment session which have not been completed (but may include sessions currently in progress).

Automatic Generation of Customized Beam Queue Visualization

FIG. 1 depicts a data flow diagram 100 of a process for providing beam-sharing functionality in an integrated beam request panel. Steps 101-111 describe exemplary steps comprising the process 100 depicted in FIG. 1 in accordance with the various embodiments herein described. In one embodiment, the process 100 is implemented in whole or in part as computer-executable instructions stored in a computer-readable medium and executed in a computing device.

At step 101, a user-actuation in an integrated beam request panel is received as input. In one embodiment, the integrated beam request panel may be instantiated in a plurality of computing devices in a facility, such as a treatment facility implementing a shared beam system. The user-actuation may be received, for example, in a beam request user-interface of the integrated control panel. In one embodiment, the beam request user-interface comprises a graphical component—such as a button, key, or toggle—that allows the user (through a user-input device such as a keyboard, or mouse, or through touch-screen functionality, for example) to submit a request to use a beam in the shared beam system. According to one aspect of the claimed subject matter, the shared beam system may be a shared proton beam treatment system, and the beam may comprise a proton beam of the shared proton beam treatment system, although the claimed subject matter may be well suited to the management of other shared or limited resource systems.

According to an aspect of the claimed subject matter, a user of the integrated-beam request panel may, for example, perform a user-actuation which submits a request to have exclusive use of the beam for a treatment session lasting a duration of time. This duration of time may be either pre-defined within the system (e.g., a default), manually customizable by the user, or automatically customized for the user (e.g., according to a treatment plan, for example). The request may be specific to a particular treatment suite or room among a plurality of suites or rooms between which the beam is shared, or a particular proton beam emitter disposed in a treatment suite or room, for example.

At step 103, a priority is determined for the request submitted in step 101. According to one embodiment, the beam request user-interface may also include functionality to allow a user to elect a priority for a submitted request. Priority may be elected as a binary toggle (e.g., with or without priority), or, may be selected from a range of values corresponding to a spectrum of priorities. A user may elect a prioritized request based on the patient or target of the beam. For example, the urgency of a patient's condition, the patient's (dis)comfort, treatment plan requirements, etc., may play a factor in the priority of a submitted request. According to further embodiments, the beam request user-interface also includes functionality to allow a user to select a scope of the treatment that the beam will be used for. The scope of the treatment may include, for example, a beam request for a single field, a plurality of independent fields, or a group of associated fields. These fields correspond to one or more treatment fields in a treatment session, as pre-defined by a treatment plan for a patient of proton therapy treatment, for example. The number of treatment fields requested by a request may impact the calculation of the duration of the treatment session, which is described in greater detail below.

At step 105, the request for use of the shared beam submitted in step 101 is appended to a beam queue with other yet-unfulfilled requests previously submitted for the shared beam from other instances of the integrated request panel, within the same treatment facility, for example. The position in the beam queue may be dependent on the priority elected by the user at step 101 and determined at step 103. For example, if no priority is elected by the user for the request, the request may be appended to the end of the beam queue. Alternatively, in some embodiments, any beam request with priority has precedence over all other beam requests without priority. According to such embodiments, if priority is elected by the user, the request may be appended to the first position of the beam queue behind the last request with priority, and ahead of every other requests without priority. Requests with the same priority may be arranged chronologically—that is, according to the order the request was received by the system. In embodiments wherein priority may be expressed within a spectrum, the position in the queue may be determined by comparing the representative priorities and ordering the queue according to priorities of the beam request.

At step 107, a customized visualization of the beam queue is generated and displayed in the instance of the beam request panel at step 107. The customized visualization of the beam queue may be implemented as, for example, graphical representations of each request in the beam queue. The graphical representations of each request may provide means of identification, such as the room or user corresponding to each request. According to embodiments, instances of the integrated request panel may include a display panel, in which the visualization of the beam queue is displayed. The beam display panel may also be dynamically generated and displayed for a user once a beam request is submitted by the user (e.g., at step 101). The beam queue may be customized for the user by specifically identifying (e.g., emphasizing) the position of the user's beam request in the beam queue relative to other requests. The identification may consist of visually distinguishing the graphical representation of the user's beam request from other beam requests, by size, color, form, or other visual indicia. Accordingly, each beam queue visualization will be customized to emphasize a different beam request in the beam queue. The beam queue is dynamically updated whenever a subsequent beam request or a prior beam request is added or removed (e.g., when a beam request is canceled). The position in the beam queue for a user's request may be adjusted as a result of additional beam requests, such as when a request with higher priority is added or removed. The customized visualization of the beam queue for every instance of the integrated beam request panel is dynamically adjusted to conform the most current order in the beam queue.

According to further embodiments, the beam display may also include with a customized visualization of the beam queue, the priorities of other requests in the beam queue, the scope of any beam requests (e.g., single, multiple, or group fields) submitted by the user corresponding to the instance of the integrated beam request panel and beam display, and a customized indicator of the estimated time remaining until the user's request for usage of the shared beam may be fulfilled. The estimated time remaining may also be calculated by, for example, tracking the average duration of each fulfilled beam request and multiplying the derived duration by the number of requests ahead of the user's request, and the time remaining in the request currently being fulfilled (if applicable).

For implementations wherein the estimated time remaining is automatically generated according to treatment plan information, a treatment calculation engine may be employed which receives as input the data corresponding to each user's beam request (e.g., the scope or number of fields in the request). The calculation engine can then reference pre-defined historical data corresponding to the expected duration for treatment sessions with a similar or equivalent scope. Alternatively, the calculation engine may be configured to reference the particular treatment plan (e.g., from a communicatively coupled resource such as a database) to determine the information corresponding to the particular treatment session (e.g., dosage, duration), and calculate an expected duration for each of the present and intervening requests in the beam queue. The estimated time remaining may thereafter be expressed as the sum of the expected durations for each present and intervening requests in the beam queue.

Finally, at step 109, usage of the shared beam is distributed according to the order of the beam queue, when each treatment session is completed, the system may verify the current order in the beam queue such that any recent updates to the beam queue may be reflected.

Integrated Beam Request Interface

Figure 2:
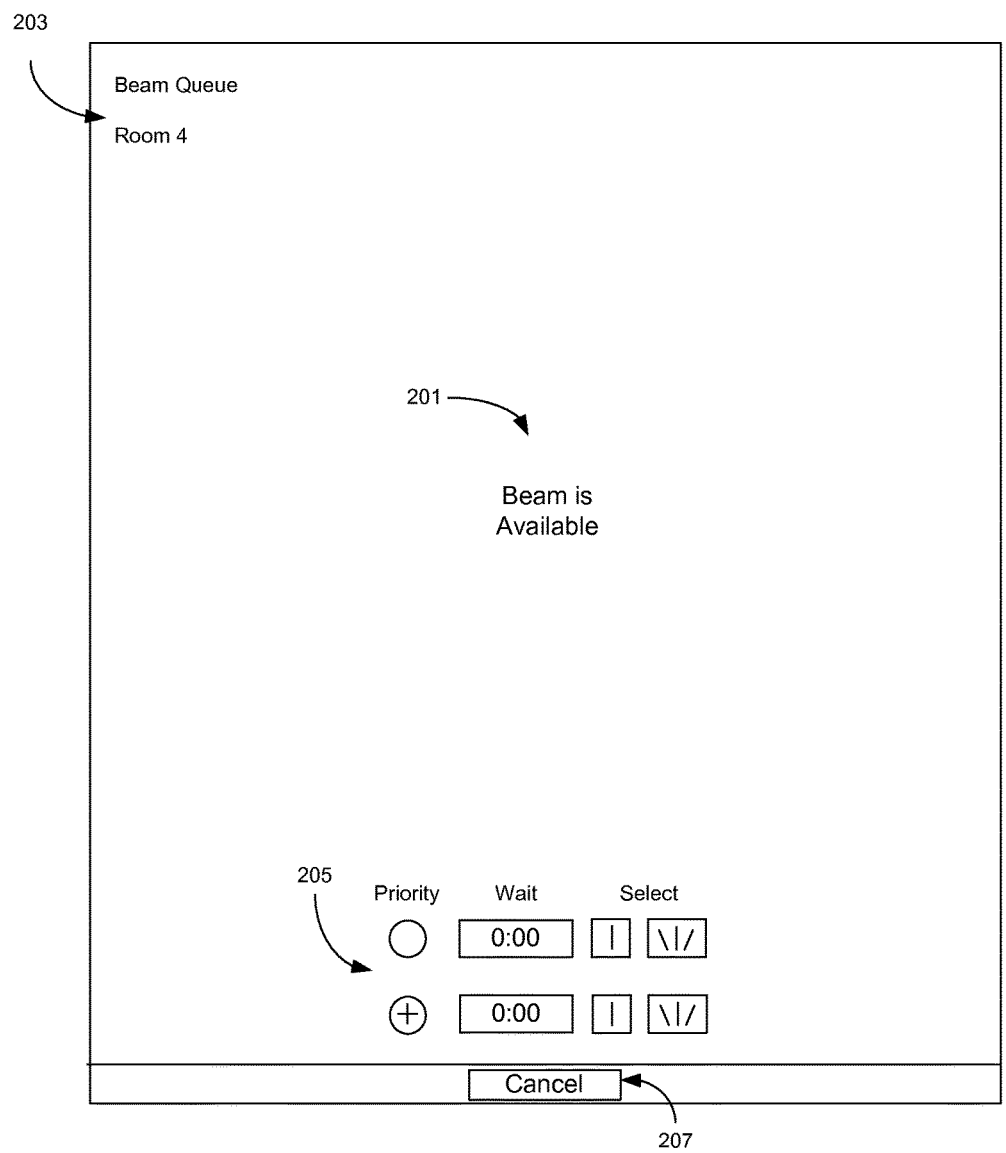
FIG. 2 depicts an example user interface of an integrated beam sharing control panel while no active beam requests are in the beam queue, in accordance with embodiments of the present disclosure.

With reference now to FIGS. 2-7, example graphical user interfaces of the beam request panel are herein described. In an embodiment, the beam sharing panel displays a graphical depiction of which beam requestors have currently active beam requests and information corresponding to the participants in the beam queue. As presented in FIG. 2, user interface 200 depicts the beam request interface when a patient or target of the beam is prepared for a treatment session while no active beam requests are in the beam queue. As depicted, user interface 200 includes a visualization of the beam queue 201, a user indicator 203, and user-input buttons 205, 207. As depicted in FIG. 2, when the beam queue is empty, the visualization of the beam queue 201 may indicate to the user that the beam is available. As depicted, the explicit message "Beam is Available" is shown. However, other graphical indicia may be used instead to express that the beam is currently unoccupied, such as alternate messages, icons, and/or displays.

As presented in FIG. 2, the user indicator 203 may display the current status of users of the terminal (the computing device executing the present instance of the beam request interface). For example, an identification of the particular user or terminal accessing the system may be displayed. According to various embodiments, the terminals may correspond to particular locations in a facility (e.g., treatment rooms). FIG. 2 depicts such an embodiment, as the user indicator 203 displays the room corresponding to the terminal (e.g., "Room 4"), and the name of the display being presented (e.g., "Beam Queue").

User-input buttons 205 and 207 are configured to respond to user-actuations to perform designated functions and/or display information, and to allow one-action beam requests. As presented in user interface 200, the user may submit a request to use the shared beam through beam request panel 205. As depicted, beam request panel 205 allows the user to specifically select the parameters of a beam request. For example, the user may be able to select with specificity whether the beam request is prioritized (indicated in FIG. 2 with the plus "+" sign), and whether the beam request is for a single field (indicated as the single vertical bar) or multiple fields (multiple bars). The user can formulate a request by actuating on the single field or multiple field buttons, with or without priority, with just a single user actuation (click). User actuation may be graphically acknowledged in the panel 205 by changing the appearance of the icon or field actuated. For example, the colors of the selected icon may be reversed, or the size of the icon may be modified, etc. Selecting an icon may automatically deselect the other icons, according to some embodiments. When any of the beam request buttons 205 is actuated, the beam request is submitted to the system and appended to the beam queue at the appropriate position, depending on the user's elected level of priority.

Once a beam request has been issued by the user, action button 207 (e.g., "Cancel" button 207) may be actuated if the user desires to cancel the beam request. As with beam request buttons 205, a single user actuation—such as a click—can be used to cancel the beam request. In some embodiments, action button 207 appears, or becomes enabled only when the user issues a beam request.

In still further embodiments, priority may be implemented according to a spectrum, and automatically calculated per beam request. That is, once information regarding a beam request is received by the system—during a prior step when a patient's information and/or treatment plan may be referenced—priority for that particular beam request is automatically calculated (via a calculation engine, for example), and ordered in the system. The information used by the system to calculate a priority may include various factors, including treatment type, treatment scope, patient data (age, infirmity, emergency), other exigent circumstances, etc. According to such embodiments, priority may not require manual election. Once the priority is determined, the position in the beam queue for the beam request based on the calculated priority is visible to the beam requestor. In some embodiments, non-clinical beam requests may be specified, and added and viewed in the queue, along with clinical beam requests. Non-clinical beam requests may include, for example, beam requests for research, education, servicing, etc. According to a further embodiment, non-clinical beam requests may be automatically assigned lower priority than clinical requests, and are added automatically without priority. Accordingly, non-clinical requests may not require user election of non-priority according to such embodiments.

According to further embodiments, the estimated wait times corresponding to a request is also displayed for each level of priority. The estimated wait time may be calculated, by a calculation engine, according to various factors. These factors include, but are not limited to: the position of the treatment room/beam requestor in the queue, or the position that the beam requestor would be if a request were submitted immediately; indicated priority of the beam request and other beam requestors currently in the queue; treatment plan-specific factors (e.g., machine accessory changes, number of treatment fields/layers/spots to be treated); type or scope of treatment; required machine activity (beam-switching, layer-switching, gantry movement). In one embodiment, the estimated wait time can be displayed as a countdown timer (e.g., in minutes and seconds). In further embodiments, in addition to, or as an alternative to displaying the estimated wait time as a countdown timer, further treatment status information may be displayed which indicates the remaining wait time. This information may include the indicated progress (as a percentage, for example) of the beam treatment session currently being performed. Other information may include the completion of steps in a sequence of steps or an achievement of a milestone. These steps or milestones may correspond to, for example, patient preparation being completed, a treatment position being verified, operation (generation) of a beam, and the conclusion of a field treatment. In all embodiments, the estimated wait time display may be updated dynamically, to reflect additions or modifications to the queue as they are submitted. When the beam queue is empty, as depicted in FIG. 2, the wait time may be listed as 0. When requests are added or removed to the beam queue, the wait time may be updated to reflect the change.

Figure 3:
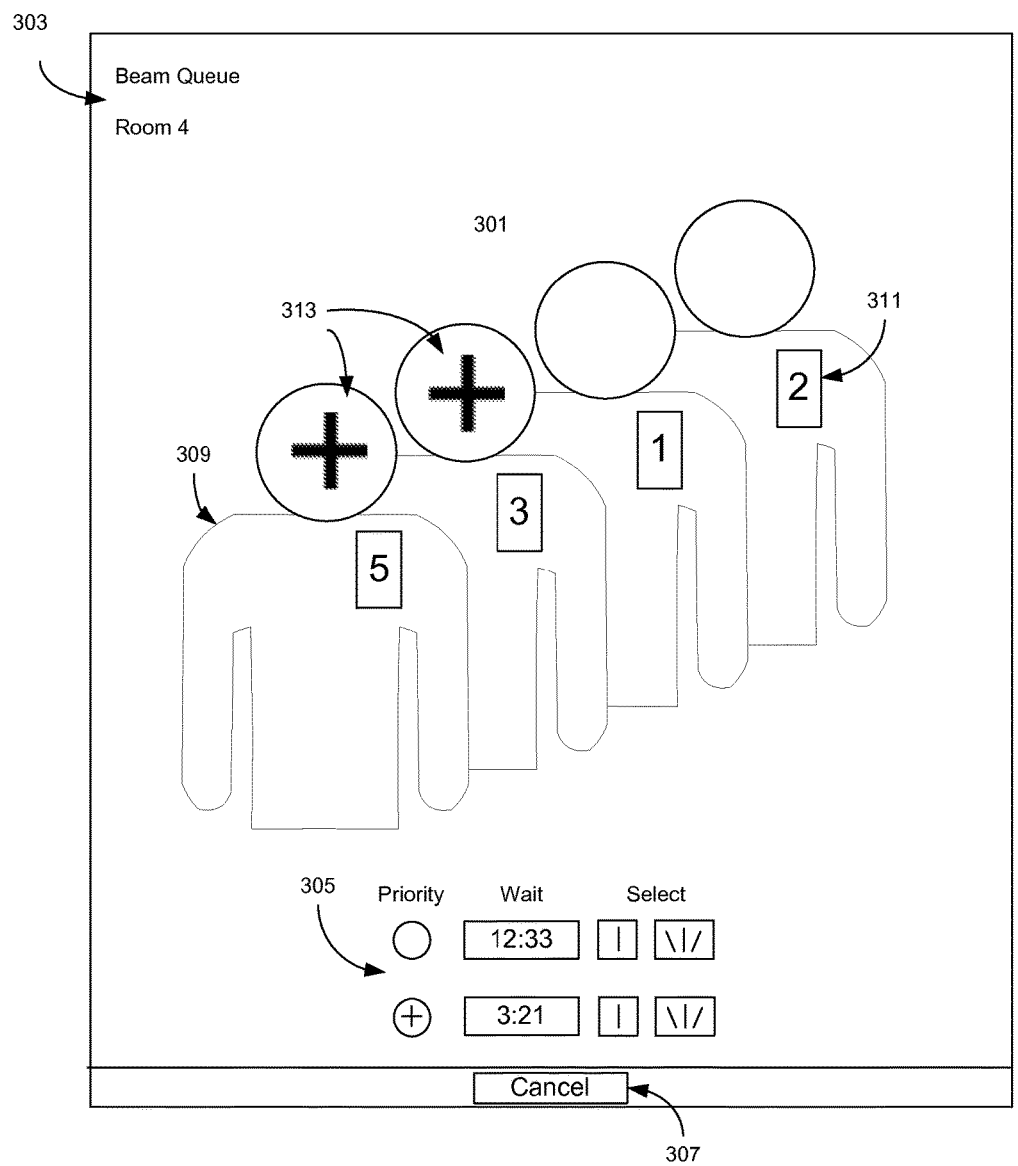
FIG. 3 depicts an example user interface of an integrated beam sharing control panel when the beam queue is populated and no beam request has been submitted from the viewing terminal, in accordance with embodiments of the present disclosure.

FIG. 3 depicts an example user interface 300 when the beam queue is populated and no beam request has been submitted from the viewing terminal. As depicted in FIG. 3, the user interface 300 includes a visualization of the beam queue 301. The visualization of the beam queue 301 graphically represents the respective positions in the beam queue for one or more submitted beam requests. This representation may be expressed in a variety of implementations.

According to an embodiment, a human silhouette 309 with associated indicators represents each beam request in the beam sharing panel user interface 300. According to some embodiments, the silhouette is depicted with a notation identifying the beam requestor 311. For example, the silhouette may include a graphical notation of the treatment room or suite, the treating physician, the treatment session, etc. The silhouettes may also be displayed with graphical characteristics which provide important information and/or distinctions. Requests submitted with an indicated priority, for example, may be represented graphically. As presented in user interface 300, priority may be expressed with the Plus sign 313. In further embodiments, the silhouette of the beam requestor (i.e., the user of the terminal accessing the beam queue) may be presented in a color or appearance scheme that is distinctive from the other silhouettes in the beam queue. Each representation of the beam request in the graphical display is thus customized according to the user or beam requestor's perspective in the user interface employed by the specific beam requestor and terminal. The silhouettes are arranged according to the order in which the beam will be granted. For example, the beam requestor that currently has been granted the beam is in the front of the queue. The beam requester that will be granted the beam last is in the back of the queue. Thus, for example, as presented in FIG. 3, treatment room 5, which has been submitted with priority, currently has use of the shared beam. Treatment room 3, which also has been submitted with priority, is next in the beam queue. Treatment rooms 1 and 2, respectively, follow treatment room 3 and comprise the remainder of the beam queue.

As depicted, user interface 300 also includes a user indicator 303, a beam request panel 305, action panel 307, request identifiers 311, and priority indicators 313. Each of these elements correspond to the like numbered elements described above with respect to FIG. 2 and user interface 200. A user is able to submit a request through any actuation of the user-input buttons comprising the user-input panel 305, as described above with respect to like numbered elements of FIG. 2. Conversely, a submitted request may be similarly canceled via a single actuation of user action button 307. A request submitted would have an estimated wait time according to the priority elected (as shown). Once a request as been selected, the user's request is appended into the beam queue at an appropriate position, and the visualization of the beam queue 301 is automatically updated for all terminals, and reflected in the user indicator 303 for the viewing terminal. Likewise, a use cancellation submitted through user action button 307 would remove the user's request from the beam queue, and remove the silhouette (or other graphical representation) of the beam requestor 311 would be removed form the visualization of the beam queue 301 for all terminals, and reflected in the user indicator 303.

Figure 4:
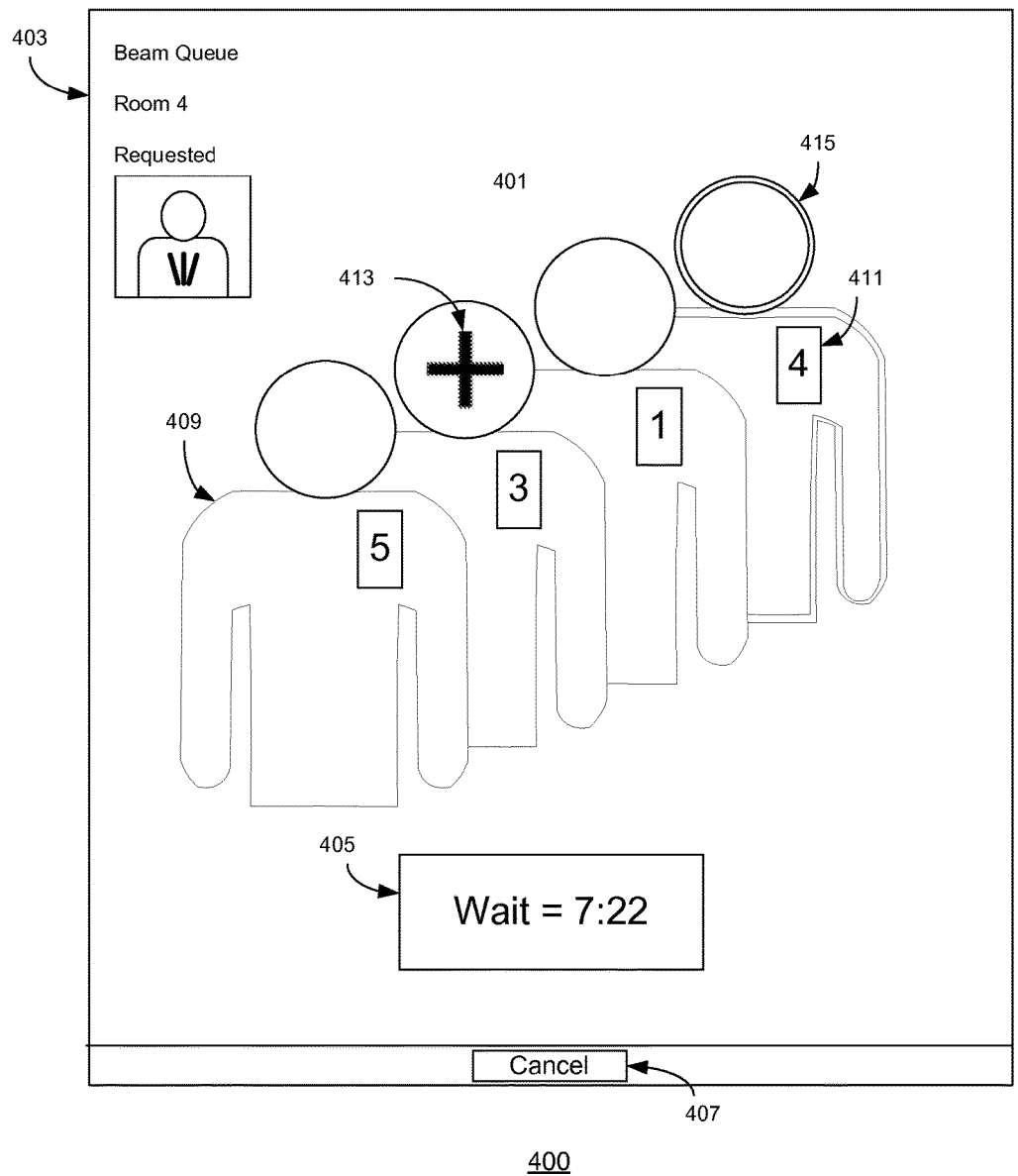
FIG. 4 depicts an example user interface of an integrated beam sharing control panel when the beam queue is populated and a beam request has been submitted from the viewing terminal, in accordance with embodiments of the present disclosure.

FIG. 4 depicts an example user interface 400 when the beam queue is populated and a beam request has been submitted from the viewing terminal. As depicted in FIG. 4, the user interface 400 includes a visualization of the beam queue 401, a user indicator 403, a wait display panel 405, action panel 407, request identifiers 411, and priority indicators 413, corresponding to similarly number elements and described with respect to previous Figures (e.g., FIG. 3). As shown, the visualization of the beam queue 401 has been updated to append the position of the request submitted by the user through the viewing terminal. As described previously, the user's position in the beam queue (e.g., the silhouette of the beam requestor) may be presented in a color or appearance scheme that is distinctive from the other silhouettes in the beam queue. As presented in FIG. 4, an outline of the silhouette 415 of the requesting user may be implemented to distinguish the silhouette from other requests in the beam queue. Beam requestors using other terminals would see a different silhouette outlined (i.e., the silhouette corresponding to their respective position in the beam queue). As such, each visualization of the beam queue 401 is customized according to the terminal viewing the beam queue.

As shown in FIG. 4, the user indicator 403 has been updated to provide that a beam has been requested, with an icon which notifies the scope of the request. According to one embodiment, the icon corresponds to the icon selected by the user to determine the scope of a submitted beam request. User interface 400 also includes a wait display panel 405 which provides an estimated time until the request of the viewing terminal can be granted. As depicted in FIG. 4, the wait display panel 405 may be implemented as a countdown timer. Finally, the user may be able to cancel the request by actuating the action button 407, which would remove the user's request from the beam queue, and automatically arrange the remaining requests accordingly, update the visualization of the beam queue 401 for all terminals, and update the user indicator 403 for the viewing terminal.

Figure 5:
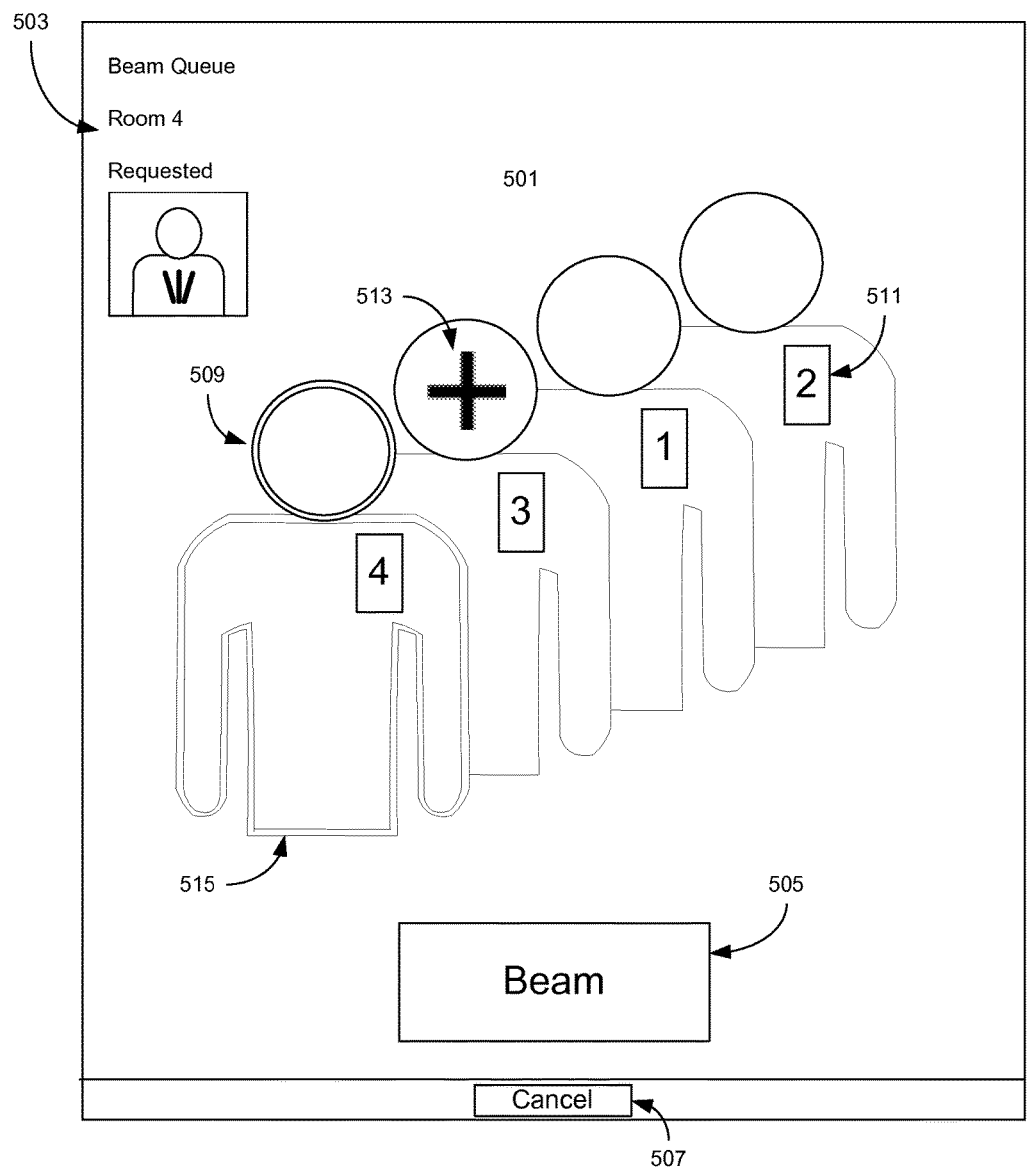
FIG. 5 depicts an example user interface of an integrated beam sharing control panel when the beam queue is populated and the beam request for the viewing terminal has been granted, in accordance with embodiments of the present disclosure.

FIG. 5 depicts an example user interface 500 when the beam queue is populated and the beam request for the viewing terminal is capable of being granted (e.g., the beam queue is empty, or the beam request is at the front of the beam queue). As depicted in FIG. 5, the user interface 500 includes a visualization of the beam queue 501, a user indicator 503, action panel 507, request identifiers 511, and priority indicators 513 corresponding to similarly number elements and described with respect to previous Figures (e.g., FIGS. 3 and 4). As shown, the visualization of the beam queue 501 has been updated to reflect that the position of the request submitted by the user is at the front of the beam queue. As presented in FIG. 5, the outline of the silhouette 515 of the requesting user (identified with the user identifier 511) may be implemented to distinguish the silhouette from other requests in the beam queue. Priority of the request is also exhibited through priority indicator 513. As shown in FIG. 5, user interface 500 also includes a display of when the beam has been granted to the viewing terminal. The user may be able to cancel the request by actuating the action button 507, which would remove the user's request from the beam queue, and automatically arrange the remaining requests accordingly, update the visualization of the beam queue 501 for all terminals, and update the user indicator 503 for the viewing terminal.

According to one embodiment, the display panel and user interface may be implemented in a proton treatment console comprising one or more in-room monitoring displays. The display panel may be used to manage and display requests from multiple treatment suites for use of a single shared proton beam. Through the user interface of the display panel, a user is able to request the beam, and be provided visualized key aspects relating to current proton beam requests and use. Functionality of the display panel may include (but are not limited to): graphical integration of key controls and displays for a beam sharing-queue; graphical visualizations of pending requests in the order in which the requests will be served, adjusted by stated priority; displays of calculated, customized wait times for each treatment suite; displays of the selected priority for each request in the beam sharing queue; displays of the wait times corresponding to both priority and normal beam requests; graphical reminders of the priorities and scope of user-requests may also be displayed in the user interface. In further embodiments, the display panel may also provide either or both visual and auditory notifications of the achievement of certain milestones, either related to current treatment sessions or alerts related to imminent treatment session stages.

Figure 6:
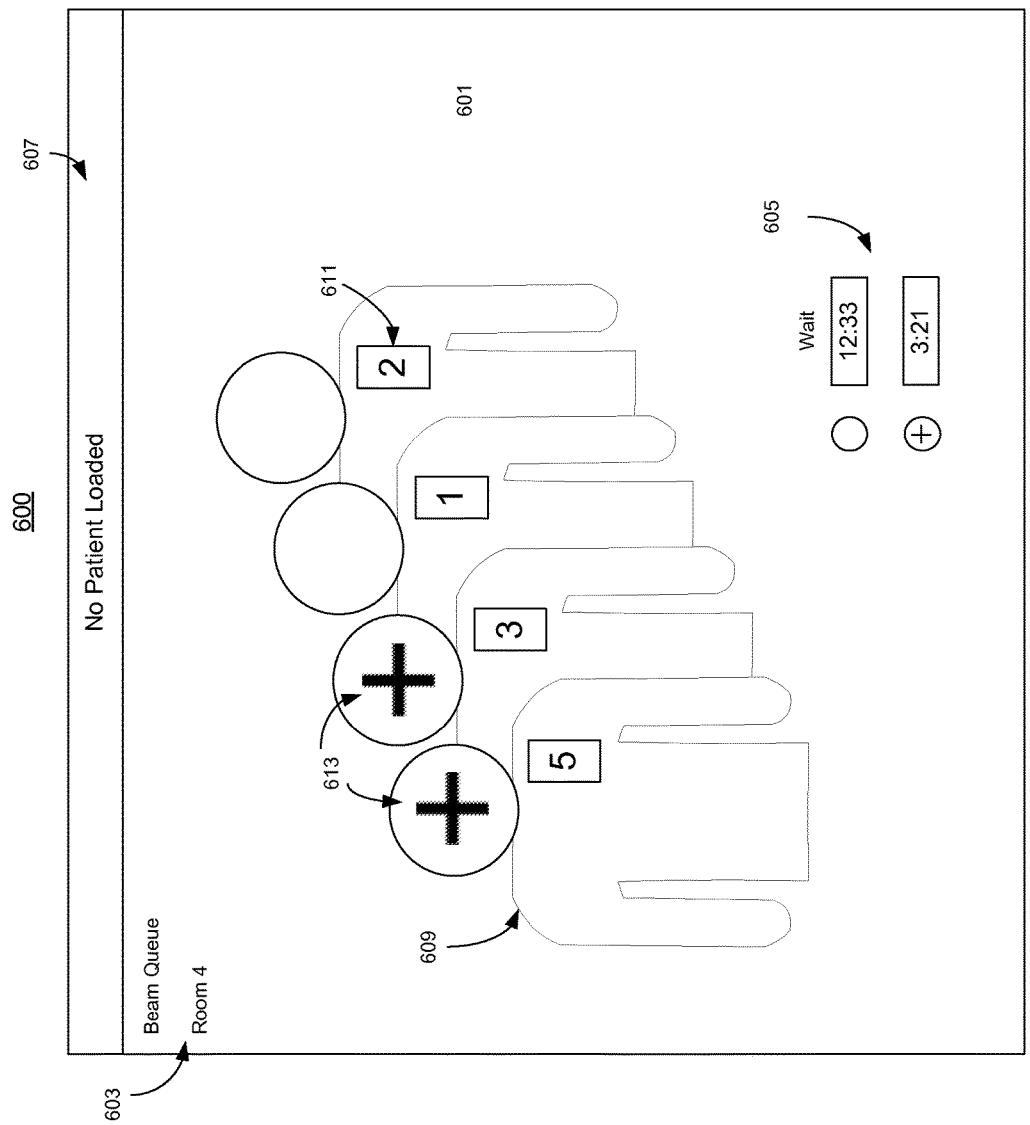
FIG. 6 depicts an example user interface of an in-room monitor comprised in an integrated beam sharing display panel, in accordance with embodiments of the present disclosure.

FIG. 6 depicts an example user interface 600 of an in-room monitor comprised in an integrated beam request panel, such as a proton treatment console. As depicted in FIG. 6, the user interface 600 includes a visualization of the beam queue 601, a user indicator 603, a beam request timer 605, and patient status 607. Patient status 607 provides a notification to the user that no patient (or treatment subject) file is loaded at the viewing terminal for this treatment room. User indicator 603, treatment room or user representations 609, request identifiers 611, and priority indicators 613 correspond to like numbered elements (e.g., elements 303, 309, 311, and 313 respectively) described above with respect to FIG. 3 and user interface 300. In one embodiment, in-room monitors may be implemented as a display of the current beam queue. As such, the beam request timer 605 may not be operable to submit a beam request, but instead, provides a display of current estimated waiting times for submitted beam requests. According to such an implementation, there are no icons for the user to select from to indicate the scope of a beam request (e.g., a single field or multiple fields).

Figure 7:
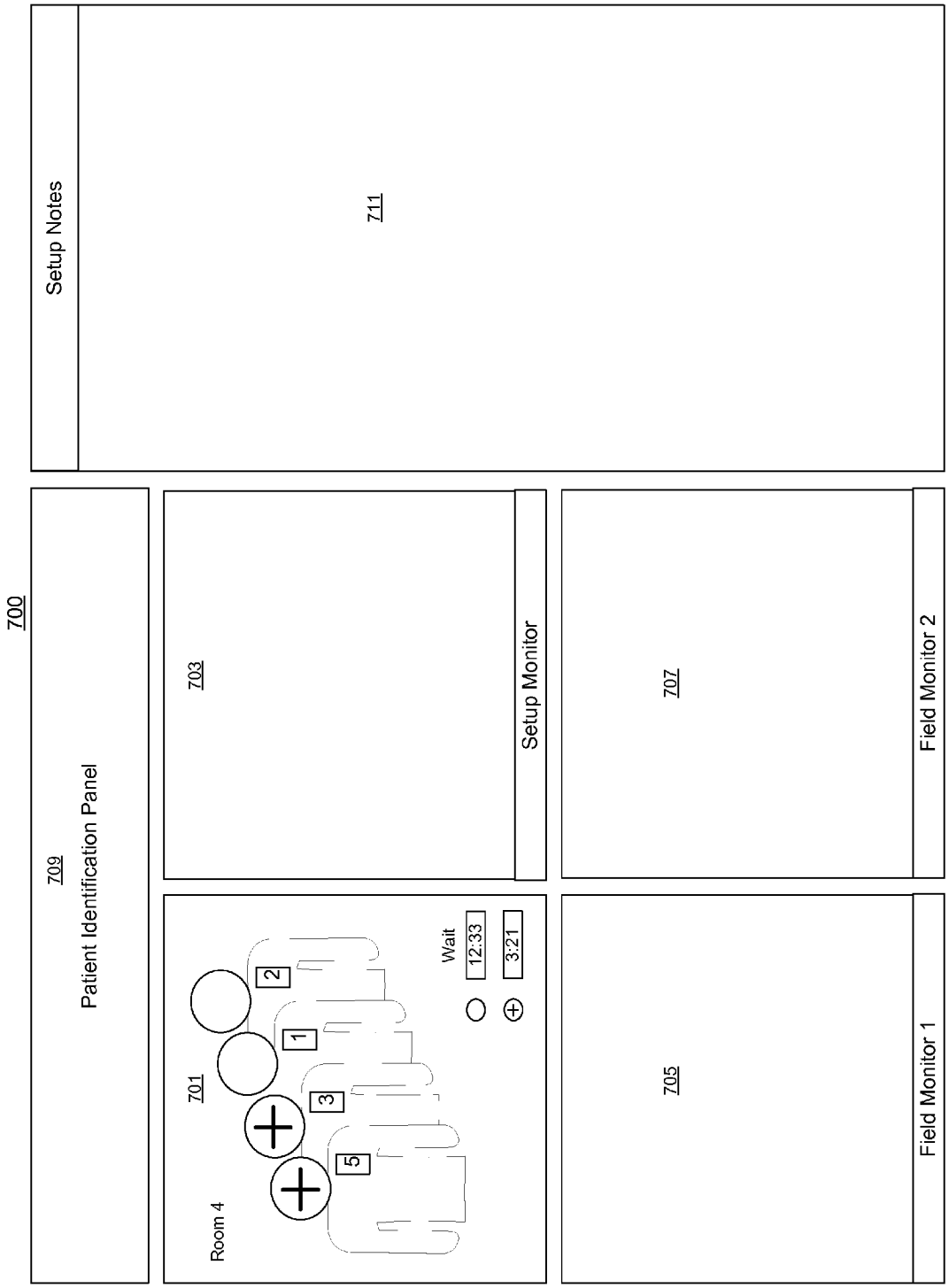
FIG. 7 depicts an example user interface comprising a composite of multiple panels displayed during the preparation period for a patient, in accordance with embodiments of the present disclosure.

According to further embodiments, user interface 600 may be presented in the integrated beam request panel separately, or as one of a plurality of panels presented during or in anticipation of preparing a patient or subject to receive treatment from a shared beam. FIG. 7 depicts such an embodiment—wherein the user interface 600 is one panel (e.g., panel 701) of a composite of multiple panels displayed during the preparation period for a patient. As depicted in FIG. 7, other display elements useful to prepare a patient or subject for beam application may be shown. These other display elements provided by the beam sharing panel may include an identification panel 709 corresponding to the patient, such as the treatment room, therapist, patient, treatment session, etc. for which the beam request is to be fulfilled. Further display elements may include in-room monitoring of a patient (e.g., the patient's position). As depicted in FIG. 7, set-up monitor (monitor display 703) and field monitors 1 and 2 (monitor display 705, 707) are presented to verify patient preparation and procedures, such as positioning the patient properly and with the proper treatment accessories and immobilization devices. An additional panel (setup notes panel 711) can list assorted preparation notes that the beam requestor (e.g., radiologist, oncologist, etc.) may refer to in order to prepare the patient for beam delivery.

Alternatively, the panel may be integrated and adapted for use with any therapy setting with a shared or finite therapeutic resource, and where more than one potential consumer of the resource can request a usage of the shared resource. Additionally, the display panel may be integrated and adapted for use with any resource sharing situation where a resource requestor can self-request and be identified as having a particular position (or priority) in a request queue. For embodiments wherein a resource is granted only for pre-set durations of time, the estimated time remaining may be calculated simply by adding the number of requests ahead of the user's request in the beam queue, multiplied by the duration of time. According to embodiments wherein a user is able to submit a desired duration of the resource usage along with the resource request, the estimated time remaining for a user's pending request may be calculated by finding the sum of the requested durations for each request preceding the user's request in the resource queue, in addition to the request currently being fulfilled (if applicable), minus the duration already elapsed in the current session. Requests submitted without specifying a duration may be attributed with a default duration or the average duration of previously fulfilled requests, for example. Still further embodiments can provide privacy benefits such as anonymous or proxy identities for public displays. Alternatively, other requesting users may have identities masked.

By utilizing the systems and methods described above, various critical functions for proton beam management in a shared beam facility may be performed. These functions—all of which can be performed within a single, integrated user-interface—include visualization of the beam queue, submission of requests for the beam for treatment, estimations of when the request will be fulfilled and cancellations of the request. As many (if not all) of these functions may be requested by the user through single actuations, a user is able to intuitively and efficiently perform these requisite functions for themselves, as well as monitor the use of the shared beam by other users in the system.

Although the subject matter has been described in language specific to structural features and/or processological acts, it is to be understood that the subject matter defined in the appended claims is not necessarily limited to the specific features or acts described above. Rather, the specific features and acts described above are disclosed as example forms of implementing the claims.

What is claimed is:

1. A system comprising:
    a plurality of integrated beam request panels, an integrated beam request panel of the plurality of integrated beam request panels being configured to execute:
        a beam request interface operable by a user to submit a beam request for use of a shared proton beam into a beam request queue, and to select a priority for the beam request from a plurality of priorities;
        a beam request display operable to display, in a graphical user interface, a beam request queue comprising an arranged order of beam requests submitted from the plurality of integrated beam request panels, an estimated time until the shared proton beam is available for a beam request for each priority of the plurality of priorities prior to a submission of the beam request, an indication of a position in the beam request queue once the beam request is submitted, and an estimated time until the shared proton beam will be available for the beam request submitted from the beam request interface of the corresponding integrated beam request panel; and
    a particle accelerator configured to generate the shared proton beam and to distribute the shared proton beam to a plurality of treatment rooms in a sequence based on the beam request queue.

2. The system according to claim 1, wherein an integrated beam request panel further comprises a calculation engine configured to estimate the time until the shared proton beam is available for a beam request submitted through the beam request interface of the integrated beam request panel.

3. The system according to claim 1, wherein the beam request display of an integrated beam request panel is further operable to display an indication that the shared proton beam is available for the beam request submitted through the beam request interface of the integrated beam request panel.

4. The system according to claim 1, wherein the beam request interface of an integrated beam request panel is further operable to submit a priority for a beam request submitted through the beam request interface.

5. The system according to claim 1, wherein the beam request display of an integrated beam request panel is further operable to display a priority corresponding to each beam request in the beam queue.

6. The system according to claim 1, wherein the shared proton beam comprises a shared proton treatment beam used to perform a proton treatment session in a treatment room of the plurality of treatment rooms.

7. The system according to claim 6, further comprising:
    a plurality of communicatively coupled computing devices are distributed among the plurality of treatment rooms.

8. The system according to claim 7, wherein a beam request for use of the shared proton beam comprises a beam request for usage of the shared proton beam in the treatment room comprising the computing device executing the integrated beam request panel.

9. The system according to claim 6, wherein the proton treatment session comprises directing the shared proton treatment beam at a field of a plurality of treatment fields, the plurality of treatment fields comprising regions disposed within a target treatment subject.

10. The system according to claim 9, wherein the shared proton beam has a corresponding adjustable dosage.

11. The system according to claim 10, wherein the dosage of the shared proton beam is adjusted based on a treatment plan devised for the target treatment subject.

12. The system according to claim 11, wherein the plurality of treatment fields comprising regions disposed within a target treatment subject correspond to the treatment plan devised for the target treatment subject.

13. A method for implementing an integrated beam-request interface, the method comprising:
    displaying, in a graphical beam request interface of an integrated beam request panel, an estimated time until a shared proton beam is available for a beam request for each priority of a plurality of priorities prior to a submission of the beam request;
    receiving, as input, a user actuation in the beam request interface the user actuation comprising a first request for usage of a shared treatment beam;
    determining a priority from the plurality of priorities corresponding to the first request for usage of the shared treatment beam;
    appending the first request to a position in a beam queue comprising a plurality of requests for usage of the shared treatment beam based on the priority of the first request;
    generating a visualization of the beam queue;
    displaying the visualization of the beam queue in a display panel of the integrated beam-request panel; and
    allocating usage of the shared treatment beam according to the beam queue,
    wherein the integrated beam-request panel comprises a first instance of a plurality of instances of the integrated beam-request panel executed on a plurality of computing devices in a plurality of treatment rooms.

14. The method according to claim 13 further comprising:
    receiving, as input, a user actuation in a beam-request interface of a second instance of the integrated beam-request panel, the user actuation comprising a second request for usage of the shared treatment beam, the second request having a higher priority than the first request;
    re-ordering the beam queue such that an order of the beam queue indicates that the second request is to be fulfilled before the first request;

dynamically adjusting the visualization of the beam queue in each instance of the plurality of instances of the beam-request interface to reflect the re-ordered beam queue; and allocating usage of the shared treatment beam according to the re- ordered beam queue.

15. The method according to claim 13, wherein the generating a visualization of the beam queue comprises automatically generating a customized visualization for each instance of the integrated beam-request panel.

16. The method according to claim 15, wherein the automatically generating a customized visualization for each instance of the integrated beam-request panel comprises automatically generating a customized visualization for each beam-request interface that includes at least one of the following pieces of information:

a respective position of any beam requests submitted by a current user of the beam-request interface in the beam queue;

an estimated time remaining until the current user of the beam-request interface is granted usage of the shared treatment beam;

an established priority of any beam requests submitted by a current user of the beam-request interface in the beam queue; and a scope of any beam requests submitted by a current user of the beam-request interface in the beam queue.

17. The method according to claim 16, wherein the scope of a beam request comprises one of: a beam request for a single field, a beam request for a plurality of single fields, or a beam request for a group of fields, the group of fields comprising a plurality of associated fields.

18. A non-transitory computer readable medium containing program instructions embodied therein for causing a computer system to synchronize management of a shared treatment beam among a plurality of distributed display panels, the program instructions comprising: instructions to implement an instance of a beam-request interface; instructions to display, in a graphical beam request interface of an integrated beam request panel, an estimated time until a shared proton beam is available for a beam request for each priority of a plurality of priorities prior to a submission of the beam request; instructions to receive as input, a user actuation of the instance of the beam-request interface, the user actuation corresponding to a first request for usage of the shared treatment beam; instructions to determine a priority corresponding to the first request for usage of the shared treatment beam; instructions to automatically append, in a beam queue, the first request for usage of the shared treatment beam; instructions to automatically generate a visualization of the beam queue for each instance of a plurality of instances of the beam-request interface; and instructions to automatically distribute usage of the shared treatment beam according to the beam queue, wherein the integrated beam-request panel comprises a first instance of a plurality of instances of the integrated beam-request panel executed on a plurality of computing devices in a plurality of treatment rooms.

19. The non-transitory computer readable medium according to claim 18 further comprising:

instructions to receive, as input, a user actuation in a beam-request interface of a second instance of the integrated beam-request panel, the user actuation comprising a second request for usage of the shared treatment beam, the second request having a higher priority than the first request;

instructions to re-order the beam queue such that an order of the beam queue indicates that the second request is to be fulfilled before the first request;

instruction to dynamically adjust the visualization of the beam queue in each instance of the plurality of instances of the beam-request interface to reflect the re-ordered beam queue; and instructions to allocate usage of the shared treatment beam according to the re-ordered beam queue.

20. The system according to claim 1, wherein the beam request display is further operable to display an arranged order of beam requests submitted as a plurality of silhouettes with additional graphical indicators arranged according to an order of the position in the beam request queue.

21. The system according to claim 1, wherein the beam request interface is further operable by a user to select between a single field and a plurality of fields to submit as a scope of treatment corresponding to a the beam request.

22. The system according to claim 1, wherein further the beam display interface displays a scope of treatment corresponding to at least one beam request in the beam request queue.

23. A system comprising:

a plurality of integrated beam request panels, an integrated beam request panel of the plurality of integrated beam request panels being configured to execute:

a beam request interface operable by a user to submit a beam request for use of a shared beam into a beam request queue, and to select a priority for the beam request from a plurality of priorities;

a beam request display operable to display, in a graphical user interface, a beam request queue comprising an arranged order of beam requests submitted from the plurality of integrated beam request panels, an estimated time until the shared beam is available for a beam request for each priority of the plurality of priorities prior to a submission of the beam request, an indication of a position in the beam request queue once the beam request is submitted, and an estimated time until the shared beam will be available for the beam request submitted from the beam request interface of the corresponding integrated beam request panel; and a particle accelerator configured to generate the shared beam and to distribute the shared beam to a plurality of rooms in a sequence based on the beam request queue.

24. A method comprising:

displaying, in a graphical beam request interface of an integrated beam request panel, an estimated time until a shared beam is available for a beam request for each priority of a plurality of priorities prior to a submission of the beam request, the shared beam is generated by a particle accelerator;

receiving, as input, a user actuation in the beam request interface the user actuation comprising a first request for usage of a shared beam;

determining a priority from the plurality of priorities corresponding to the first request for usage of the shared beam;

appending the first request to a position in a beam queue comprising a plurality of requests for usage of the shared beam based on the priority of the first request;

generating a visualization of the beam queue;

displaying the visualization of the beam queue in a display panel of the integrated beam-request panel; and allocating usage of the shared beam according to the beam queue, wherein the integrated beam-request panel comprises a first instance of a plurality of instances of the integrated beam-request panel executed on a plurality of computing devices in a plurality of rooms.

* * * * *